United States Patent [19]
Roelse et al.

[11] 4,102,647
[45] Jul. 25, 1978

[54] REMOVAL OF CONDENSATES FROM LIGHT GASEOUS STREAMS

[75] Inventors: Adriaan Roelse, Domburg; Barteld Hendrik van der Ley, Middelburg, both of Netherlands

[73] Assignee: Total Raffinaderij Nederland N.V., Rotterdam, Netherlands

[21] Appl. No.: 741,993

[22] Filed: Nov. 15, 1976

[30] Foreign Application Priority Data
Nov. 20, 1975 [NL] Netherlands .................... 7513573

[51] Int. Cl.$^2$ .................... G01N 31/08; B01D 53/02
[52] U.S. Cl. .................... 23/232 R; 55/74; 73/23.1
[58] Field of Search .......... 23/232 R, 254 R; 55/97, 55/528, 29, 35, 74; 73/23.1, 29

[56] References Cited
U.S. PATENT DOCUMENTS
3,727,379  4/1973  Bijleveld et al. ............... 55/74 X OTHER PUBLICATIONS
Gas Chromatography Abstracts, 1970, p. 112, #602.

Primary Examiner—Robert M. Reese
Attorney, Agent, or Firm—Haseltine, Lake & Waters

[57] ABSTRACT

A process for removing condensates from light gaseous streams comprises passing the stream over an oleophilic substance, that is, a substance which retains liquid hydrocarbon compounds. Said substance is preferably an aromatic polymer such as a polystyrene cross-linked with a mixture of divinyl benzene and ethyl-vinyl benzene.

The process is particularly applicable to the analysis of gaseous compounds, such as water, in said gaseous streams, where the presence of such condensates can render the analysis results erroneous.

There is also described a gas analyzer which comprises a means for removing such condensates which means employs such an oleophilic substance.

8 Claims, 3 Drawing Figures

REMOVAL OF CONDENSATES FROM LIGHT GASEOUS STREAMS

BACKGROUND OF THE INVENTION

This invention relates to a process for removing condensates from light gaseous streams and in particular is applicable to gaseous streams which are subjected subsequently to analysis. The invention also relates to applications of this process and to apparatus for carrying out the process.

The light gaseous streams which are used, for example, in chemical, petroleum or petrochemical processes, such as gaseous streams composed principally of hydrogen and/or hydrocarbons having 1 to 6 carbon atoms, can be contaminated during these processes by condensates which often need to be removed. These condensates, whose exact chemical nature is not precisely known, are found particularly in the recycle gas of a catalytic hydro-reforming process. In particular, these condensates would comprise aromatic compounds and polyolefins.

These condensates are especially undesirable when analysing light gaseous currents, in which they can interfere with the determination of a gaseous compound. This is the case, for example, when analysing a gaseous current containing a small proportion of water, which has to be maintained close to a given value. Sometimes it is even absolutely necessary that the gas does not contain any water at all. This is particularly the case during the polymerisation of an alpha olefin in the presence of hydrogen using a catalyst containing organo-aluminum. Likewise it is sometimes desirable for the gas to contain a very small proportion of water. This is the case in certain catalytic processes in which optimum activity of the catalyst is obtained only in the presence of such a small proportion of water. This is so, in particular, in the processes for hydroreforming hydrocarbons.

In this instance, in order to check whether the proportion of water is in fact equal to the desired value, it is necessary to carry out a continuous analysis of the gaseous streams entering the hydroreforming unit. In the course of comparative analyses of such gaseous streams, the Applicants have established that continuous-analysis apparatus gives erroneous results after a certain period of operation; a situation which becomes even more serious when, in reliance on an erroneous result, an incorrect adjustment could be made to the proportion of water in the light gaseous stream and the activity of a catalyst, for example, could be seriously reduced. The Applicants have discovered that these erroneous results are caused by the presence of condensates in the gaseous streams, which are deposited on the measuring instruments.

It is particularly difficult to remove condensates contained in light gaseous streams, since the size of the condensate particles is often very small, in the order of one tenth of a micron, and these particles are not retained by conventional filters.

SUMMARY OF THE INVENTION

This invention relates, firstly, to a process for removing condensates from a light gaseous stream and is applicable, in particular, to gaseous streams which are subsequently subjected to analysis, which process comprises passing the light gaseous stream over an oleophilic substance. In this specification the term "oleophilic substance" means a substance which retains liquid hydrocarbon compounds.

Secondly, this invention relates to the application of the process as defined above to the removal of condensates from a light gaseous stream composed principally of a substance chosen from the group made up of hydrogen, nitrogen, oxygen and ethylene.

Thirdly, this invention relates to analysers which put into practice the above-defined process and which are intended, in particular, for measuring the water content of light gaseous streams.

In the process according to the invention the oleophilic substances over which the gaseous stream is passed preferably comprises a polymerisation product of a monomer having an aromatic ring, e.g. styrene.

Polymerisation products of monomers having an aromatic ring can comprise homopolymers, or modified or nonmodified copolymers of these monomers. In particular, the Applicants have successfully used a polystyrene cross-linked with a mixture of divinyl benzene and ethyl-vinyl benzene.

The oleophilic substances preferably have a particle size of from 0.15 to 0.30 mm, but preferably greater than 0.175 mm, so as to retain the condensates and allow the desired products to pass.

Although the method by which the oleophilic substances retain condensates is not clearly explicable, they behave in the manner of a filter.

It can be advantageous to subject the oleophilic substances to a silanization treatment, for example with trimethylchlorosilane $(CH_3)_3SiCl$. Since the chlorine reacts with the hydroxy groups of the oleophilic substance, the latter would thus comprise on its surface $(CH_3)_3SiO$ groups and the methyl residues would retain by affinity organic compounds such as the condensates.

When it is undesirable for water to be retained by the oleophilic substance, it is necessary to subject the oleophilic substance to a prior treatment in order to eliminate polar compounds, such as molecules carrying a hydroxy group which retain water by hydrogen bonds.

This treatment may involve a first stage of extraction with reflux using a polar solvent, such as acetone, and a second stage of extraction with reflux using a non-polar solvent, such as hexane. After these extractive treatments the solvent is removed, for example by passage of a nitrogen stream at 200° C for at least 3 hours. It is preferable to keep the oleophilic substance in a nitrogen atmosphere.

The hourly spatial velocity of the gaseous stream (volume of gas passing per hour over a unit volume of substance) depends on the nature of the condensates to be retained, on their concentration and on the nature of the oleophilic substance employed.

The same applies to the pressure of the gaseous stream and to the temperature of the oleophilic substance.

The condensates which can be removed by the process according to the invention are made up of compounds having very variable molecular weight, which can be equal to or greater than 200. These compounds may, in particular, be polyolefins and aromatic condensates.

These compounds may be of aerosol type, i.e. having particles of extremely small size, in the order of one tenth of a micron.

The process according to the invention makes it possible to eliminate condensates from light gaseous streams containing up to 1000 p.p.m. of these condensates, this concentration determining the amount of oleophilic substance necessary for the removal of said condensates.

The process according to the invention can be applied to the removal of condensates in any light gaseous stream, e.g. those composed principally of hydrogen, nitrogen, oxygen or ethylene, in particular with a view to the analysis of said light streams.

In particular, it can be applied to a light gaseous stream composed mainly of hydrogen and/or hydrocarbons having 1 to 6 carbon atoms and, optionally, one or more other gaseous compounds. Such other gaseous compound may be, for example, water present in a lower proportion than that corresponding to saturation in the prevailing conditions of pressure and temperature.

A gaseous stream composed mainly of hydrogen may be, for example, a recycling gas from a hydrocarbon-conversion unit and, in particular, catalytic hydroreforming, which contains at least 70% by volume of hydrogen and should not contain more than 300 p.p.m. of water.

The process according to the invention can be carried out in any apparatus necessitating the purification of a light gaseous stream containing condensates.

This is the case, for instance, in apparatus for analysing light gaseous streams, wherein the presence of condensates hinders the determination of any gaseous compound which, in particular, may be water.

A first type of water analyser comprises an analyser containing a substance capable of retaining water, such as phosphorus anhydride, the water retained then being electrolysed, measurement of the amount of current required for this electrolysis making it possible to determine the quantity of water which is present.

Another type of apparatus for analysing water in gases comprises an analyser which uses in combination:
(a) a first supply of gas to be analysed, said first supply being provided with a filter intended to retain, in particular, particles of solids and oils;
(b) a second supply of dry reference gas, said second supply being provided with a gas-drying device;
(c) two cells for measuring the amount of water and each comprising a quartz-crystal oscillator;
(d) a system for distributing alternately gas to be analysed and dry reference gas into each of the two measuring cells.

The dry reference gas may comprise a portion of the gas to be analysed, from which the water has been removed by drying.

The principal of this analyser lies in comparing the variations in frequencies of two sensitive members, in the form of quartz-crystal hygroscopic oscillators, in the presence of the gas containing water to be analysed. The water vapour contained in the gas is in turn adsorbed and desorbed rapidly on each crystal, which gives rise to differences in mass and, therefore, differences in the frequencies. Each crystal is alternately exposed to the gas containing water and to the dry reference gas. When one of the crystals adsorbs water, the other is dried by the dry gas and vice-versa. The adsorption of water by a crystal decreases its vibration frequency, whereas the frequency of the other crystal increases whilst drying. Comparison of the two frequencies makes it possible to determine the concentration of water in the gas.

Generally, these different types of analysers give good results. However, if the gas to be analysed contains condensates which are liable to be deposited on the measuring cells, then their operation may be affected thereby. In fact, the presence of this layer of condensates on the measuring cells distorts the analysis result and can be particularly inconvenient when, in the course of a process, it is desirable to maintain substantially constant a particular concentration of water in a gaseous stream. A result which is too low can, for example, lead to the addition of an excessively large quantity of water into the gaseous stream, thus interfering with the course of the process.

In carrying out the process according to the invention in analysers, particularly in water-analysers, the supply system for gas to be analysed is equipped with a device for removing condensates from said gas to be analysed, said device containing an oleophilic substance, such as that used in the process according to the invention.

In the case of water-analysers, the oleophilic substance shall have undergone a prior treatment intended to eliminate polar compounds.

The actual conformation of the device for removing condensates may be of any type desired.

For example, two elements in parallel can be used. The Applicants have used with particular success a device similar to the "heatless drier" marketed by the PUREGAS EQUIPMENT CORP., with an original filling. This form of embodiment does not constitute a restriction of the invention. It will be described in detail below.

BRIEF DESCRIPTION OF THE DRAWING

Reference will now be made by way of example to the accompanying drawings, in which.

DESCRIPTION OF THE PREFERRED EMBODIMENTS

Figure 1:
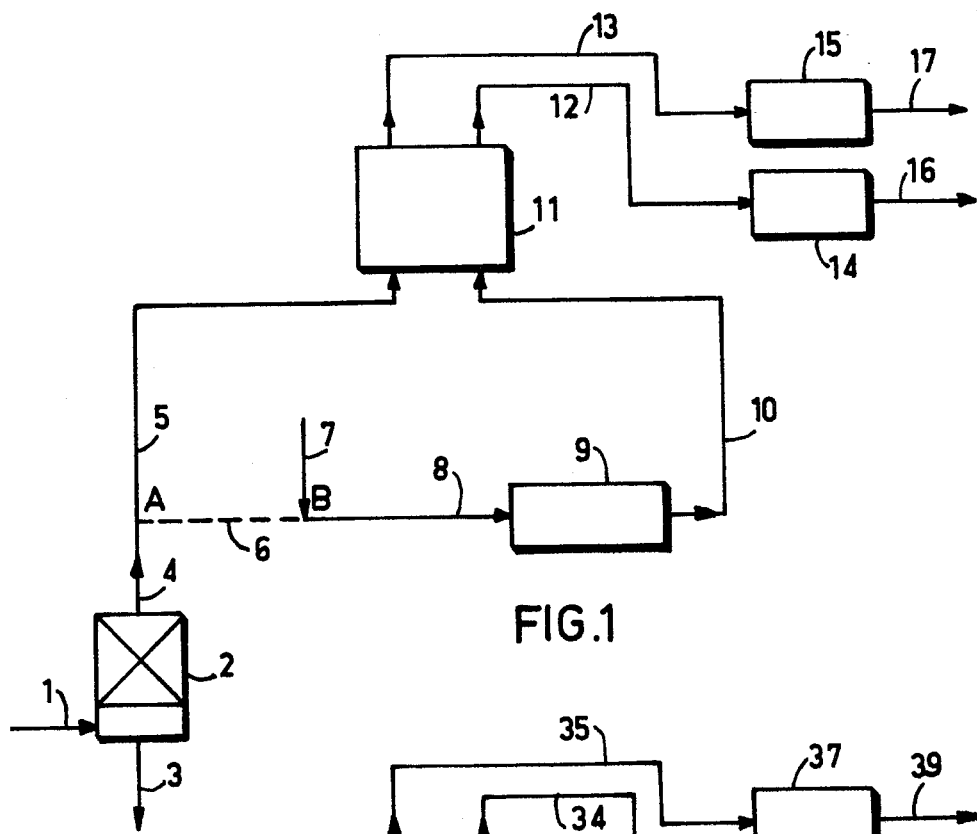
FIG. 1 is a simplified diagram of a water-analyser of known type, whose measuring cells take the form of quartz-crystal oscillators.

In the analyser shown in FIG. 1 the gaseous stream to be analysed is admitted through line 1 into a filter 2 designed to retain, in particular, solid and oil particles. It is possible to discharge through line 3 particles retained by the filter.

The gaseous stream emerging from the filter 2 through line 4 can be separated into two portions at the point A, one portion, conducted along the line 5, serving as the gas to be analysed and the other portion, conducted along the line 6, serving as the reference gas after drying.

All of the gaseous current issuing from the filter 2 may be used as gas for analysis, the reference gas being admitted in this case at point B through line 7.

The reference gas is introduced through line 8 into a drying device 9 which is designed to remove any water contained in the gas. This drying device contains a molecular sieve. The dry reference gas is then passed through line 10 into an alternating distribution system 11.

The gas to be analysed is similarly passed through line 5 into the alternating distribution system 11.

The alternating distribution system makes it possible to change over, after a given period of time, the reference gas and the gas to be analysed. These latter emerge from this system alternately through lines 12 and 13 are are conveyed to measuring cells 14 and 15 which are in the form of quartz oscillators. The difference in the oscillation frequencies is measured by an electronic device (not shown) and makes possible determination of water content of the gas being analysed.

Figure 2:
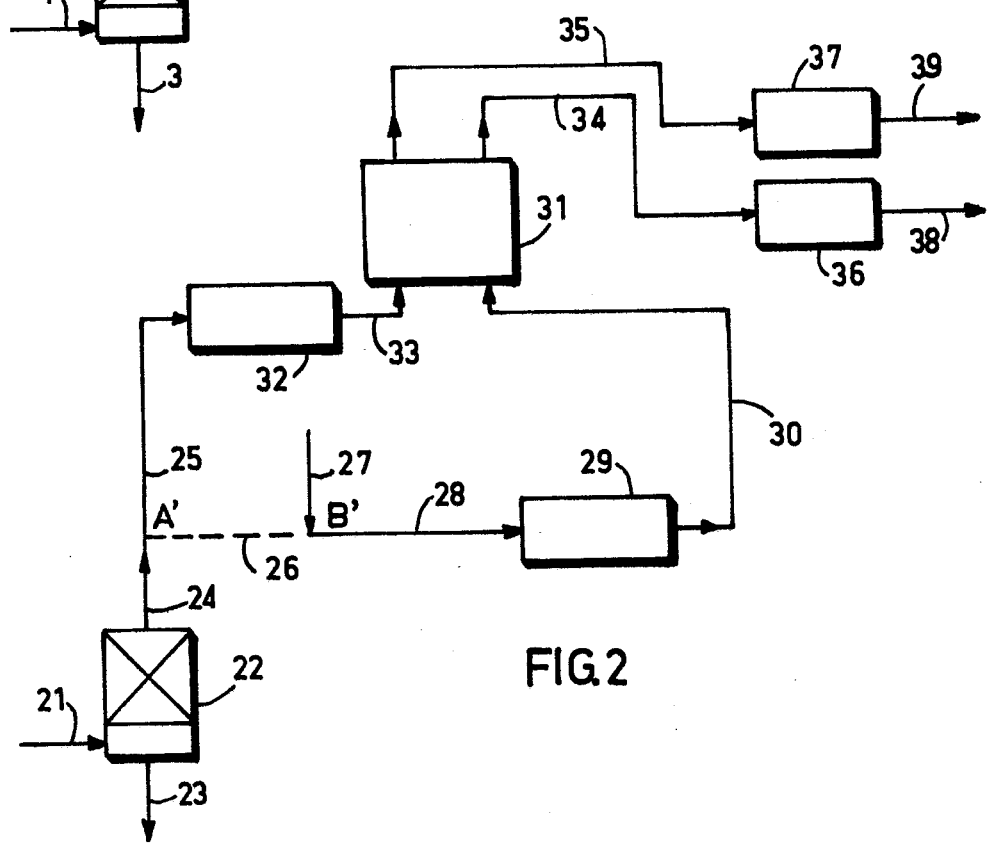
FIG. 2 is a diagram of a water-analyser putting into practice the process of the present invention and whose measuring cells like those of FIG. 1 comprise quartz oscillators but which is provided, in addition, with a condensate-removing device.

In the case of the analyser in FIG. 2, the gaseous current for analysis is admitted through line 21 into a filter 22 designed to retain, in particular, solid and oil particles. It is possible to discharge through line 23 particles retained by the filter.

The gaseous stream issuing from the filter through line 24 can be divided into two portions at the point A', one portion, conveyed along line 25, serving as the gas to be analysed and the other portion, conveyed along the line 26, serving as the reference gas after drying.

All of the gaseous stream issuing from the filter 22 may be used as gas for analysis, the reference gas being admitted in this case at the point B' through line 27.

The reference gas is introduced through line 28 into a drying device 29 designed to remove any water contained in the gas. This drying device contains a molecular sieve. The reference gas is then conveyed through line 30 into an alternating distribution system 31.

The gas to be analysed is conveyed through line 25 into a condensate-removing device 32. This device contains an oleophilic substance which has undergone prior treatment intended to eliminate polar compounds, as described hereinbefore.

The gas for analysis is then conveyed through line 33 into the laternating distribution system 31. The reference gas and the gas for analysis re-emerge therefrom through lines 34 and 35, respectively, and are conveyed to the measuring cells 36 and 37, from whence they are discharged through lines 38 and 39.

The alternating distribution system and the measuring cells are similar in all respects to those shown in and described with reference to FIG. 1.

Figure 3:
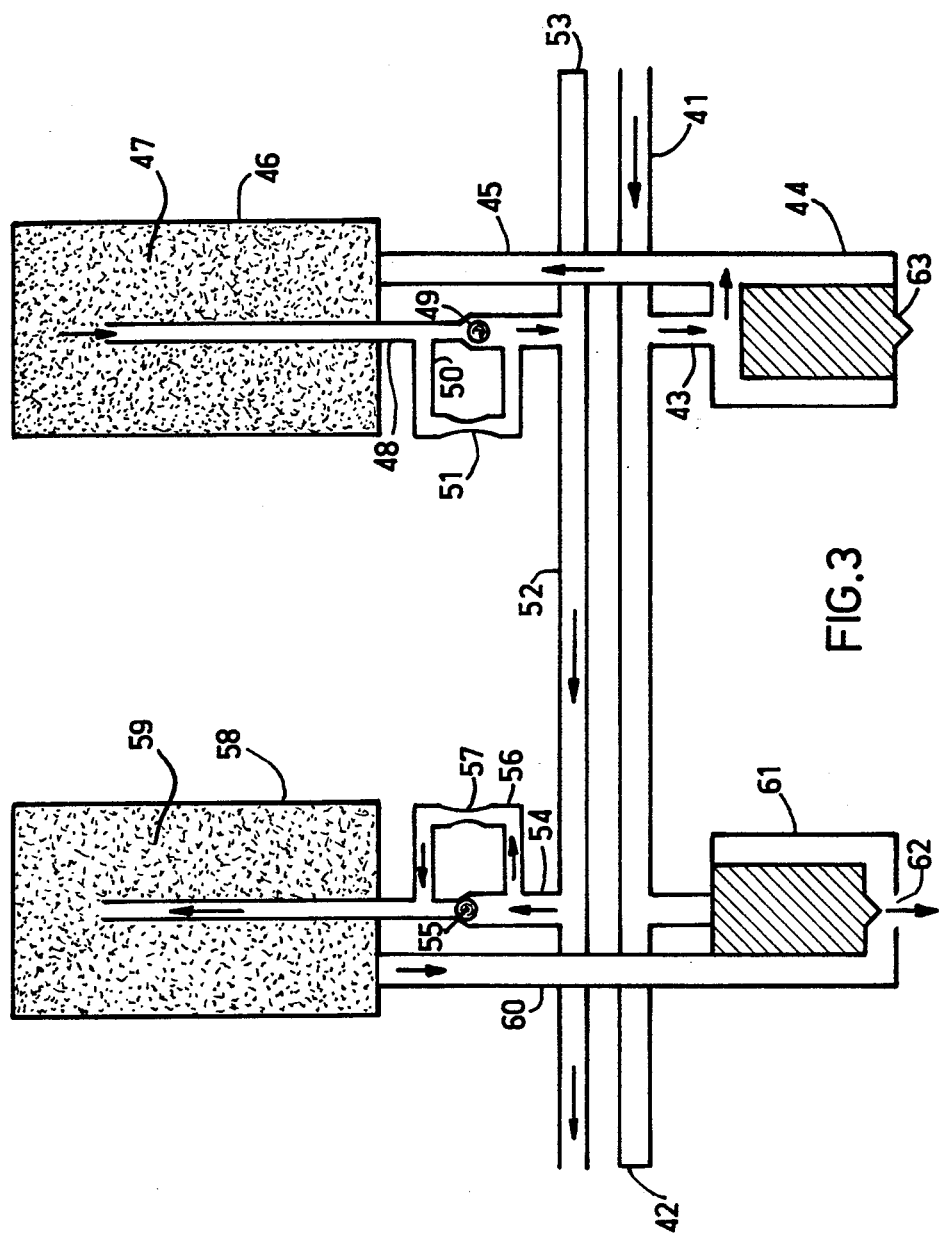
FIG. 3 illustrates a particular embodiment of a device for removing condensates in accordance with the invention.

In the condensate-removing device shown in FIG. 3 the gas to be treated is admitted into the device through line 41 whose end 42 is closed. In a first stage, the gas circulates inside the device in the direction indicated by the arrows. It enters via a line 43 into a solenoid valve 44, which is shown in its open position. It re-emerges therefrom through line 45 so as to enter a vessel 46 containing an oleophilic substance 47; this substance is designed to retain the condensates and has undergone prior treatment in order to eliminate polar compounds, as described hereinbefore.

The gas re-emerges from the housing 46 through line 48 which is provided, on the one hand, with a valve 49 which is shown in the form of a ball and is shown in the open position and, on the other hand, with a by-pass 50 incorporating a constriction 51. The gas, thus freed of condensates, is conveyed through line 52, one end 53 of which is closed, towards the alternating distribution device.

One portion of the gas, however, enters through the line 54 also provided with a valve 55, shown in the drawing in the closed position, and with a by-pass 56 incorporating a constriction 57, into a second vessel 58 containing the same substance 59 as vessel 46.

The gas then follows in this second vessel an inverse course to that followed in the first vessel. It re-emerges therefrom through the line 60 and enters the solenoid valve 61, shown in the closed position. The gas is able to leave this valve through the orifice 62.

At the end of this first stage with a cycle lasting 30 seconds, the valve 44 and the valve 49 are closed whereas the valve 55 and the valve 61 are opened, which reverses the direction of flow of the gas through the vessels, the substance 59 retaining the condensates and the substance 47 being freed of at least part of the condensates. The gas leaves the valve 44 through the orifice 63.

This device, when filled with a dessicant, such as a molecular sieve, can also be used as the drying device, designated 9 and 29 in FIGS. 1 and 2.

The invention is illustrated by the following Example.

EXAMPLE

This Example relates to the analysis of water contained in a recycling gas from a hydroreforming unit.

Two tests were carried out:

(i) a control test using a water-analyser such as that described with reference to FIG. 1.

(ii) a second test using an analyser, putting into practice the process according to the invention, as described with reference to FIG. 2.

These tests were carried out on a gaseous stream whose composition was as follows:

|  | % by volume |
|---|---|
| hydrogen | 81.0 |
| methane | 6.0 |
| ethane | 5.6 |
| propane | 4.0 |
| isobutane | 1.0 |
| normal butane | 1.0 |
| isopentane | 0.5 |
| normal pentane | 0.3 |
| hydrocarbons with 6 carbon atoms | 0.6 |
| water | 10 p.p.m. |
| condensates | 10 p.p.m. |

The rate of flow of the gaseous stream was 1500 cm$^3$ per minute and the pressure at the inlet to the analysers was 1.05 kg/cm$^2$.

The analyser carrying out the process according to the invention was equipped with a condensate-removing device in the form of a "heatless drier" containing for each element 80 cm$^3$ of a polystyrene cross-linked with a mixture of divinyl benzene and ethyl-vinyl benzene.

This cross-linked polystyrene, which is marketed under the name PORAPAK by the firm WATERS, was rendered "inert" by a surface silanization process. In order to avoid retention of water by absorption by polar compounds, the polystyrene was firstly subjected to extraction with acetone in the hot state, then with n-hexane and, finally, was conditioned in a nitrogen stream at 250° C.

This cross-linked polystyrene, which had a particle size of between 0.30 mm and 0.175 mm, had a temperature of 40° C.

The water content of the gas to be analysed was measured using conventional methods concurrently with the measurements carried out by the two analysers.

It was observed that after a period of 30 days it was necessary to change the crystals in the measuring cells of the control analyser, the former being covered with a layer of condensates which gave rise to erroneous results.

On the other hand, the analyser carrying out the process according to the invention was functioning normally 180 days after it had been set into operation.

This Example clearly demonstrates the effectiveness of the process according to the invention for the purification of light gaseous streams containing condensates.

We claim:

1. In a process for the quantitative determination of water in a light gaseous stream the improvement comprising the removal of condensates from said gaseous stream by passing said gaseous stream over an oleophilic substance, said substance comprising a polystyrene which has been cross-linked with a mixture of divinylbenzene and ethylvinylbenzene.

2. A process as claimed in claim 1 wherein said oleophilic substance has a particle size of from 0.15 to 0.30 mm.

3. A process as claimed in claim 1 wherein said oleophilic substance is one which has undergone a silanization treatment.

4. A process as claimed in claim 1 wherein said light gaseous stream consists essentially of a gas selected from the group consisting of hydrogen, nitrogen, oxygen and ethylene.

5. A process as claimed in claim 1 wherein the light gaseous stream is a recycling gas from a hydrocarbon-conversion unit.

6. A process as claimed in claim 1 wherein said hydrocarbon-conversion unit is a catalytic hydroreforming unit.

7. A process as claimed in claim 1 wherein the water is present in a proportion less than that corresponding to saturation under prevailing temperature and pressure.

8. A process as claimed in claim 1 wherein the oleophilic substance has undergone a prior treatment to eliminate polar compounds.

* * * * *